(12) United States Patent
Yang et al.

(10) Patent No.: US 8,907,120 B2
(45) Date of Patent: *Dec. 9, 2014

(54) PERFLUOROPOLYETHER-CONTAINING COMPOUNDS WITH OXALYLAMINO GROUPS

(75) Inventors: Yu Yang, Eden Prairie, MN (US); Miguel A. Guerra, Woodbury, MN (US); Richard G. Hansen, Mahtomedi, MN (US); David S. Hays, Woodbury, MN (US); Suresh S. Iyer, Woodbury, MN (US); Ramesh C. Kumar, Woodbury, MN (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 241 days.

This patent is subject to a terminal disclaimer.

(21) Appl. No.: 13/514,322

(22) PCT Filed: Dec. 22, 2010

(86) PCT No.: PCT/US2010/061801
§ 371 (c)(1),
(2), (4) Date: Jun. 7, 2012

(87) PCT Pub. No.: WO2011/082067
PCT Pub. Date: Jul. 7, 2011

(65) Prior Publication Data
US 2012/0289736 A1 Nov. 15, 2012

Related U.S. Application Data

(60) Provisional application No. 61/291,025, filed on Dec. 30, 2009.

(51) Int. Cl.
| | | |
|---|---|---|
| C07C 229/26 | (2006.01) | |
| C07C 69/62 | (2006.01) | |
| C08G 65/00 | (2006.01) | |
| C07C 231/02 | (2006.01) | |
| C08G 65/332 | (2006.01) | |
| C08G 69/40 | (2006.01) | |
| C08G 69/42 | (2006.01) | |

(52) U.S. Cl.
CPC ............ *C08G 65/007* (2013.01); *C07C 231/02* (2013.01); *C08G 65/332* (2013.01); *C08G 65/3322* (2013.01); *C08G 69/40* (2013.01); *C08G 69/42* (2013.01)
USPC .......................................... 560/168; 560/171

(58) Field of Classification Search
CPC .................................................... C07C 231/02
See application file for complete search history.

(56) References Cited

U.S. PATENT DOCUMENTS

| | | |
|---|---|---|
| 2,343,808 A | 3/1944 | Schlack |
| 3,250,807 A | 5/1966 | Fritz |
| 3,392,097 A | 7/1968 | Gozzo |
| 3,442,942 A | 5/1969 | Sianesi |
| 3,485,806 A | 12/1969 | Bloomquist |
| 3,699,145 A | 10/1972 | Sianesi |
| 3,715,378 A | 2/1973 | Sianesi |
| 3,728,311 A | 4/1973 | Park |
| 3,810,874 A | 5/1974 | Mitsch |
| 3,890,269 A | 6/1975 | Martin |
| 4,085,137 A | 4/1978 | Mitsch |
| 4,119,615 A | 10/1978 | Schulze |
| 4,661,577 A | 4/1987 | Jo Lane |
| 4,684,728 A | 8/1987 | Möhring |
| 5,026,890 A | 6/1991 | Webb |
| 5,093,432 A | 3/1992 | Bierschenk |
| 5,214,119 A | 5/1993 | Leir |
| 5,266,650 A | 11/1993 | Guerra |
| 5,276,122 A | 1/1994 | Aoki |
| 5,461,134 A | 10/1995 | Leir |
| 5,488,142 A | 1/1996 | Fall |
| 5,512,650 A | 4/1996 | Leir |
| 5,663,127 A | 9/1997 | Flynn |
| 6,313,335 B1 | 11/2001 | Roberts |
| 6,355,759 B1 | 3/2002 | Sherman |
| 6,511,721 B1 | 1/2003 | Murata |
| 6,923,921 B2 | 8/2005 | Flynn |
| 7,335,786 B1 | 2/2008 | Iyer |
| 7,371,464 B2 | 5/2008 | Sherman |
| 7,501,184 B2 | 3/2009 | Leir |

(Continued)

FOREIGN PATENT DOCUMENTS

| | | |
|---|---|---|
| EP | 1388556 | 2/2004 |
| EP | 2096133 | 9/2009 |

(Continued)

OTHER PUBLICATIONS

De Abajo, "Carbon-13 NMR Sequence Analysis. 23. Synthesis and NMR Spectroscopic Characterization of Polyoxamides with Alternating and Random Sequences of Aliphatic Diamines", Journal of Macromolecular Science, Chemistry, 1984, vol. A21, No. 4, pp. 411-426.

Gaade, "The Interaction of Diethyl Oxalate and Ethane Diamine", Recueil des Travaux Chimiques des Pays-Bas, Jan. 25, 1936, vol. 55, pp. 325-230.

(Continued)

*Primary Examiner* — Yong Chu
(74) *Attorney, Agent, or Firm* — Jean A. Lown

(57) ABSTRACT

Compounds containing at least one perfluoropolyether segment and at least two oxalylamino groups as well as methods of making these compounds are described. The compounds can be polymeric materials or can be used in the preparation of various copolymeric materials by reaction with compounds having at least two primary or secondary amino groups.

11 Claims, No Drawings

(56) References Cited

U.S. PATENT DOCUMENTS

| | | | |
|---|---|---|---|
| 7,745,653 B2 | 6/2010 | Iyer | |
| 7,883,652 B2 | 2/2011 | Leir | |
| 8,552,124 B2 * | 10/2013 | Hansen et al. | 525/474 |
| 2007/0148474 A1 | 6/2007 | Leir | |
| 2007/0149745 A1 | 6/2007 | Leir | |
| 2008/0318057 A1 | 12/2008 | Sherman | |
| 2008/0318058 A1 | 12/2008 | Sherman | |
| 2011/0092638 A1 | 4/2011 | Leir | |
| 2012/0259088 A1 * | 10/2012 | Iyer et al. | 528/343 |
| 2012/0264890 A1 | 10/2012 | Hansen | |
| 2012/0271025 A1 | 10/2012 | Hays | |

FOREIGN PATENT DOCUMENTS

| | | |
|---|---|---|
| WO | WO 96/34030 | 10/1996 |
| WO | WO 2004/034139 | 4/2004 |
| WO | WO 2005/003210 | 1/2005 |
| WO | WO 2007/073502 | 6/2007 |
| WO | WO 2007/075317 | 7/2007 |
| WO | WO 2007/075802 | 7/2007 |
| WO | WO 2007/082046 | 7/2007 |
| WO | WO 2008/027594 | 3/2008 |
| WO | WO 2009/002611 | 12/2008 |

OTHER PUBLICATIONS

Gaade, "Esters of Ethane-1 : 2-Dioxamic Acid and Their Derivatives II", Recueil des Travaux Chimiques des Pays-Bas, Jan. 25, 1936, vol. 55, pp. 541-559.

Vogl, "Polyoxamides. I. Preparation and Characterization of Cyclic Oxamides", Macromolecules, Jul.-Aug. 1968, vol. 1, No. 4, pp. 311-315.

International Search Report for PCT/US2010/061801, 3 pages.

* cited by examiner

PERFLUOROPOLYETHER-CONTAINING COMPOUNDS WITH OXALYLAMINO GROUPS

CROSS REFERENCE TO RELATED APPLICATIONS

This application is a national stage filing under 35 U.S.C. 371 of PCT/US2010/061801, filed Dec. 22, 2010, which claims priority to U.S. Provisional Application No. 61/291,025, filed Dec. 30, 2009, the disclosure of which is incorporated by reference in its/their entirety herein.

TECHNICAL FIELD

Compounds containing at least one perfluoropolyether segment and at least two oxalylamino groups as well as methods of making these compounds are described.

BACKGROUND

Fluorinated polymeric materials such as those containing perfluoropolyether segments have been used in applications where low surface energy materials and/or low refractive index materials are desired.

Polymeric materials with polydiorganosiloxane segments and aminooxalylamino groups have been prepared. These polymeric materials can be used, for example, to prepare adhesive compositions and various types of polymeric films.

SUMMARY

Compounds containing at least one perfluoropolyether segment and at least two oxalylamino groups as well as methods of making these compounds are described. The compounds can be polymeric materials or can be used in the preparation of various copolymeric materials by reaction with amine compounds having at least two primary or secondary amino groups. The resulting polymeric or copolymeric materials can be used, for example, in applications where low surface energy materials and/or low refractive index materials are desired.

In one aspect, a product of a reaction mixture is provided. The reaction mixture includes a fluorinated amine and an oxalate compound. The fluorinated amine has a perfluoropolyether segment and has at least two primary amino groups, at least two secondary amino groups, or at least one primary amino group plus at least one secondary amino group. The oxalate compound is of Formula (I).

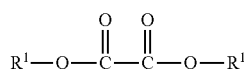

(I)

Each $R^1$ group in Formula (I) is independently an alkyl, haloalkyl, aralkyl, substituted aralkyl, alkenyl, aryl, substituted aryl, or imino of formula $-N=CR^4R^5$. The $R^4$ group is hydrogen, alkyl, aralkyl, substituted aralkyl, aryl, or substituted aryl. The $R^5$ group is alkyl, aralkyl, substituted aralkyl, aryl, or substituted aryl.

In a second aspect, a compound of Formula (II) is provided.

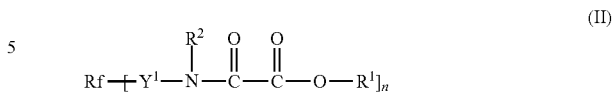

(II)

Group Rf in Formula (II) is a perfluoropolyether group. Each $Y^1$ is independently (a) a heteroalkylene, (b) an alkylene, (c) a carbonylamino linking a first group to a second group, wherein the first group and the second group are each independently an alkylene or heteroalkylene, or (d) a combination thereof. Each is independently an alkyl, haloalkyl, aralkyl, substituted aralkyl, alkenyl, aryl, substituted aryl, or imino of formula $-N=CR^4R^5$. The $R^4$ group is hydrogen, alkyl, aralkyl, substituted aralkyl, aryl, or substituted aryl. The $R^5$ group is alkyl, aralkyl, substituted aralkyl, aryl, or substituted aryl. Each $R^2$ is independently hydrogen, alkyl, aralkyl, or aryl. The variable n is an integer equal to at least 2.

In a third aspect, a compound is provided of Formula (III).

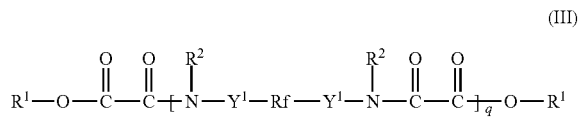

(III)

Group Rf in Formula (III) is a perfluoropolyether group. Each $Y^1$ is independently (a) a heteroalkylene, (b) an alkylene, (c) a carbonylamino linking a first group to a second group, wherein the first group and the second group are each independently an alkylene or heteroalkylene, or (d) a combination thereof. Each $R^1$ is independently an alkyl, haloalkyl, aralkyl, substituted aralkyl, alkenyl, aryl, substituted aryl, or imino of formula $-N=CR^4R^5$.

The $R^4$ group is hydrogen, alkyl, aralkyl, substituted aralkyl, aryl, or substituted aryl. The $R^5$ group is alkyl, aralkyl, substituted aralkyl, aryl, or substituted aryl. Each $R^2$ is independently hydrogen, alkyl, aralkyl, or aryl. The variable q is an integer equal to at least 1.

In a fourth aspect, a polymeric material is provided that has at least one group of Formula (IV).

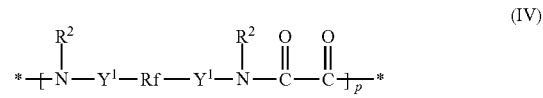

(IV)

Group Rf in Formula (IV) is a perfluoropolyether group. Each $Y^1$ is independently (a) a heteroalkylene, (b) an alkylene, (c) a carbonylamino linking a first group to a second group, wherein the first group and the second group are each independently an alkylene or heteroalkylene, or (d) a combination thereof. Each $R^2$ group is independently hydrogen, alkyl, aryl, or aralkyl. The variable p is an integer equal to at least 1. Each asterisk denotes a site of attachment to another group of the polymeric material.

The above summary is not intended to describe each disclosed embodiment or every implementation of the present invention. The description that follows more particularly exemplifies illustrative embodiments. In several places through the description, guidance is provided through lists of examples, which can be used in various combinations. In each instance, unless stated to the contrary, the recited list serves only as a representative group and should not be interpreted as an exclusive list.

DETAILED DESCRIPTION

Compounds containing at least one perfluoropolyether segment and at least two oxalylamino groups as well as methods of making these compounds are described. The compounds can be polymeric materials or can be used for the preparation of various copolymeric materials by reaction with compounds having at least two primary amino groups, at least two secondary amino groups, or at least one primary amino group plus at least one secondary amino group.

Definitions

The terms "a", "an", and "the" are used interchangeably with "at least one" to mean one or more of the elements being described.

The term "and/or" means either or both. For example, the expression X and/or Y means X, Y, or a combination thereof (both X and Y).

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, ethylhexyl, and octadecyl.

The term "alkylene" refers to a divalent group that is a radical of an alkane. The alkylene can be straight-chained, branched, cyclic, or combinations thereof. The alkylene typically has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where (CO) denotes a carbonyl group and R is an alkyl group.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, 1-propenyl, and 1-butenyl.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, naphthyl, acenaphthyl, anthraquinonyl, phenanthryl, anthracenyl, pyrenyl, perylenyl, and fluorenyl.

The term "substituted aryl" refers to an aryl substituted with one or more groups selected from halo, alkyl, haloalkyl, alkoxy, or alkoxycarbonyl.

The term "aralkyl" refers to a monovalent group of formula —R—Ar where R is an alkylene and Ar is an aryl group. That is, the aralkyl is an alkyl substituted with an aryl.

The term "substituted aralkyl" refers to an aralkyl substituted with one or more groups selected from halo, alkyl, haloalkyl, alkoxy, or alkoxycarbonyl. The aryl portion of the aralkyl is typically the group that is substituted.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "halocarbonyl" refers to a monovalent group of formula —(CO)X where (CO) denotes a carbonyl and X is halo.

As used herein, the term "imino" refers to a group of formula —N=CR$^4$R$^5$ where the R$^4$ group is hydrogen, alkyl, aralkyl, substituted aralkyl, aryl, or substituted aryl and the R$^5$ group is alkyl, aralkyl, substituted aralkyl, aryl, or substituted aryl.

The term "heteroalkylene" refers to a divalent group that includes at least two alkylene groups connected by a thio, oxy, or —NR$^2$— where R$^2$ is hydrogen, alkyl, aryl, or aralkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms. Some heteroalkylene groups are poly(alkylene oxide) groups where the heteroatoms are oxygen.

The term "perfluoropolyether" refers to divalent group of segment of formula —(C$_x$F$_{2x}$—O)$_y$— where x is an integer in the range of 1 to 10 and y is an integer equal to at least 2. The integer x is often in the range of 1 to 8, in the range of 1 to 6, in the range of 1 to 4, in the range of 2 to 4, equal to 3, or equal to 4. The integer y is often at least 3, at least 4, at least 8, at least 12, at least 16, at least 20, at least 30, at least 40, or at least 50.

The term "perfluoroalkylene" refers to an alkylene in which all of the hydrogen atoms are replaced with fluorine atoms.

The term "oxalyl" refers to a divalent group of formula —(CO)—(CO)— where each (CO) denotes a carbonyl group.

The term "oxalylamino" refers to a divalent group of formula —(CO)—(CO)—NR$^2$— where each (CO) denotes a carbonyl group and where R$^2$ is hydrogen, alkyl, aryl, or aralkyl.

The term "aminooxalylamino" refers to a divalent group of formula —NR$^2$—(CO)—(CO)—NR$^2$— where each (CO) denotes a carbonyl group and where R$^2$ is hydrogen, alkyl, aryl, or aralkyl.

The term "carbonylamino" refers to a divalent group of formula —(CO)—NR$^2$— where each (CO) denotes a carbonyl group and where R$^2$ is hydrogen, alkyl, aryl, or aralkyl.

The term "primary amino" refers to a monovalent group —NH$_2$.

The term "secondary amino" refers to a monovalent group —NHR$^3$ where R$^3$ is an alkyl, aryl, or aralkyl.

The terms "polymer" and "polymeric material" are used interchangeably and refer to materials prepared from one or more reactants (i.e., monomers). Likewise, the term "polymerize" refers to the process of making a polymeric material from one or more reactants. The terms "copolymer" and "copolymeric material" are used interchangeably and refer to polymeric material prepared from at least two different reactants.

Compounds having at least one perfluoropolyether segment and at least two oxalylamino groups are provided. These materials are typically the reaction product of a reaction mixture that includes a fluorinated amine and an oxalate compound. The number of oxalylamino groups in the compound can be varied by altering the ratio (based on equivalents) of the fluorinated amine to the oxalate compound.

The fluorinated amine, which is reacted with the oxalate compound, has a perfluoropolyether segment and has at least two primary amino groups, at least two secondary amino groups, or at least one primary amino group plus at least one secondary amino group. The fluorinated amine is often of Formula (V).

(V)

In Formula (V), Rf is a perfluoropolyether group and each $R^2$ is independently hydrogen, alkyl, aryl, or aralkyl. Each $Y^1$ is independently (a) a heteroalkylene, (b) an alkylene, (c) a carbonylamino linking a first group to a second group, wherein the first group and the second group are each independently an alkylene or heteroalkylene, or (d) a combination thereof. The variable n is an integer equal to at least 2, at least 3, or at least 4. In many embodiments, the variable n is no greater than 10, no greater than 8, no greater than 6, no greater than 4, or no greater than 3. The variable n is often in the range of 2 to 10, in the range of 2 to 6, or in the range of 2 to 4. The valency of the Rf group is equal to n. To prepare a linear reaction product, n is usually equal to 2 and Rf is a divalent group. A mixture of fluorinated amines of Formula (V) can be used.

In some embodiments of Formula (V), the fluorinated amine is of Formula (Va) with two primary amino groups.

(Va)

In some embodiments of Formula (V), the variable n is equal to 2 and the fluorinated amine is of Formula (Vb). If both amino groups are primary amino groups, the fluorinated amine is of Formula (Vc).

(Vb)

(Vc)

Each $R^2$ group in Formulas (V) and (Vb) independently can be hydrogen, alkyl, aralkyl, or aryl. Suitable alkyl groups can be linear or branched and typically contain 1 to 10 carbon atoms, 1 to 8 carbon atoms, 1 to 6 carbon atoms, or 1 to 4 carbon atoms. Suitable aryl groups typically include those having 6 to 12 carbon atoms. The aryl group is often phenyl. Suitable aralkyl groups include those having an alkyl group with 1 to 10 carbon atoms substituted with an aryl group having 6 to 12 carbon atoms. Exemplary aralkyl groups often include an alkyl having 1 to 10 carbon atoms or 1 to 4 carbon atoms substituted with a phenyl.

The Rf group in Formula (V) is a perfluoropolyether group having a segment of formula —$(C_xF_{2x}O)_y$— where x is an integer in the range of 1 to 10 and y is an integer equal to at least 2. The integer x is often in the range of 1 to 8, in the range of 1 to 6, in the range of 1 to 4, in the range of 2 to 4, equal to 3, or equal to 4. The integer y is often at least 3, at least 4, at least 8, at least 12, at least 16, at least 20, at least 30, at least 40, or at least 50. In some specific perfluoropolyether groups, x is equal to 3 and the perfluoropolyether group includes a poly(hexafluoropropylene oxide) segment. That is, Rf often includes a segment of formula —$(C_3F_6O)y$- and each —$C_3F_6O$— group in the segment can be linear or branched.

Some exemplary Rf groups are of formula

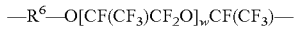

where $R^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variable w is an integer in the range of 1 to 35, in the range of 1 to 30, in the range of 1 to 20, in the range of 1 to 10, or in the range of 1 to 5.

Other exemplary Rf groups are of formula

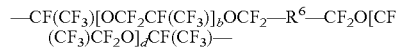

where $R^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variables b and d are both integers with a sum in the range of 0 to 35, in the range of 1 to 35, in the range of 2 to 35, in the range of 0 to 30, in the range of 1 to 30, in the range of 2 to 30, in the range of 0 to 20, in the range of 1 to 20, in the range of 2 to 20, in the range of 0 to 10, in the range of 1 to 20, in the range of 2 to 15, in the range of 4 to 15, or in the range of 2 to 10. In some exemplary Rf groups, $R^6$ is equal to —$CF_2CF_2$— and the sum of b and d is in the range of 2 to 20, in the range of 4 to 20, or in the range of 4 to 15. The preparation of the corresponding dimethyl esters of these Rf groups is described, for example, in U.S. Pat. No. 3,250,807 (Fritz et al.) such as Example IV.

Yet other exemplary Rf groups are of formula

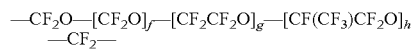

where the variables f, g, and h are integers with a sum in the range of 0 to 35, in the range of 1 to 35, in the range of 2 to 35, in the range of 3 to 35, in the range of 3 to 30, in the range of 3 to 20, in the range of 3 to 15, or in the range of 3 to 10. Exemplary materials are commercially available from Solvay Solexis (West Deptford, N.J.) under the trade designation FOMBLIN Z-DEAL.

Still other exemplary Rf groups are of one of the following formulas

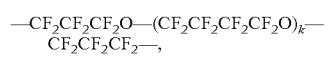

where k is a variable in the range of 0 to 35, in the range of 1 to 30, in the range of 1 to 25, in the range of 1 to 20, in the range of 1 to 15, or in the range of 1 to 10. The corresponding dimethyl esters of these Rf groups can be prepared by direct fluorination of an organic precursor that is then reacted with methanol. This preparation method is described in U.S. Pat. No. 5,488,142 (Fall et al.) such as Example 2 and in U.S. Pat. No. 5,093,432 (Bierschenk et al.) such as in Example 4.

Each $Y^1$ in Formula (V) is independently (a) a heteroalkylene, (b) an alkylene, or (c) a carbonylamino linking a first group to a second group, wherein the first group and the second group are each independently an alkylene or heteroalkylene, or (d) a combination thereof. When group $Y^1$ includes a carbonylamino group linking a first group to a second group, the resulting linked group can be of formula —$Y^{1a}$—(CO)—$NR^2$—$Y^{1a}$— where each $Y^{1a}$ is independently an alkylene or heteroalkylene. Multiple such groups can be linked together such as, for example, —$Y^{1a}$—(CO)$NR^2$—$Y^{1a}$—(CO)$NR^2$—$Y^{1a}$— and —$Y^{1a}$—(CO)$NR^2$—$Y^{1a}$—(CO)$NR^2$—$Y^{1a}$—(CO)$NR^2$—$Y^{1a}$—.

Although any suitable heteroalkylene group can be used, $Y^1$ (or $Y^{1a}$) often contains oxygen heteroatoms (i.e., oxy groups). The heteroalkylene can have at least 2 carbon atoms and at least one heteroatom, at least 4 carbon atoms and at least one heteroatom, at least 6 carbon atoms and at least one heteroatoms, at least 10 carbon atoms and at least two carbon atoms, or at least 20 carbon atoms and at least three or at least four heteroatoms. Any suitable alkylene group can be used for $Y^1$ (or $Y^{1a}$). The alkylene group can have at least 1 carbon atoms, at least 2 carbon atoms, at least 3 carbon atoms, at least 4 carbon atoms, at least 6 carbon atoms, at least 10 carbon atoms, or at least 20 carbon atoms.

Some exemplary fluorinated amines of Formula (V) include, but are not limited to, those of formula Rf—(CH$_2$OC$_3$H$_6$NH$_2$)$_2$ or Rf—(CH$_2$OC$_2$H$_4$NH$_2$)$_2$ where Y$^1$ is a heteroalkylene. Other exemplary fluorinated amines include, but are not limited to, those of formula Rf—(CH$_2$CH$_2$NH$_2$)$_2$ or Rf—(CH$_2$NH$_2$)$_2$ where Y$^1$ is an alkylene.

In other embodiments of Formula (V), the fluorinated amine is of Formula (VI).

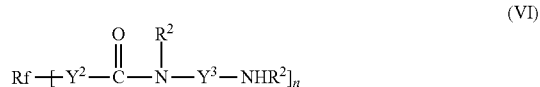
(VI)

The group Y$^1$ in Formula (V) is equal to —Y$^2$—(CO)—NR$^2$—Y$^3$— in Formula (VI). The variable n as well as the groups Rf and R$^2$ are the same as in Formula (V). Each Y$^2$ is independently a single bond, heteroalkylene, alkylene, or combination thereof. Each Y$^3$ is independently a heteroalkylene, alkylene, or combination thereof. Although any suitable heteroalkylene can be used for either Y$^2$ or Y$^3$, the heteroalkylene often has oxygen heteroatoms. Each heteroalkylene includes at least 2 carbon atoms and at least one heteroatom, at least 4 carbon atoms and at least one heteroatom, at least 6 carbon atoms and at least one heteroatom, at least 10 carbon atoms and at least two heteroatoms, or at least 20 carbon atoms and at least three or at least four heteroatoms. Suitable alkylene groups for Y$^2$ have at least one carbon atom while suitable alkylene groups for Y$^3$ have at least two carbon atoms. Exemplary alkylene groups for either Y$^2$ or Y$^3$ can have at least 2 carbon atoms, at least 4 carbon atoms, at least 6 carbon atoms, at least 10 carbon atoms, at least 12 carbon atoms, at least 18 carbon atoms, or at least 20 carbon atoms.

In some embodiments of Formula (VI), the variable n is equal to 2 and the fluorinated amine is of Formula (VIa). If the amino groups are both primary amino groups, the fluorinated amine is of Formula (VIb).

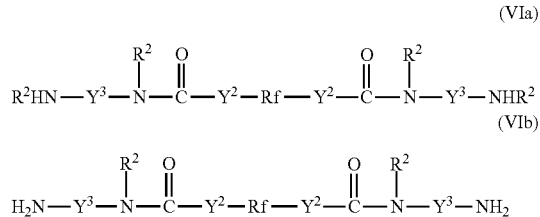

In some more specific embodiments of Formula (VIa) and (VIb), the Y$^2$ group is a single bond and the fluorinated amine is of Formula (VIc) and (VId), respectively.

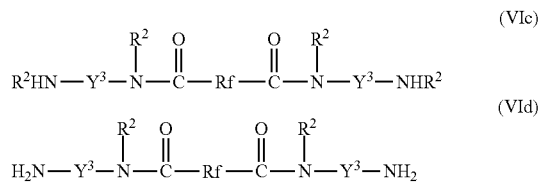

Some even more specific compounds of Formula (VIa), (VIb), (VIc), and (VId) include a Rf group of formula

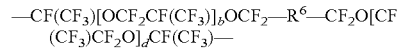

where R$^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variables b and d are both integers with a sum in the range of 0 to 35, in the range of 1 to 35, in the range of 2 to 35, in the range of 0 to 30, in the range of 1 to 30, in the range of 2 to 30, in the range of 0 to 20, in the range of 1 to 20, in the range of 2 to 20, in the range of 0 to 10, in the range of 1 to 20, or in the range of 2 to 10. In some exemplary Rf groups, R$^6$ has 2 to 6 carbon atoms and the sum of b and d is in the range of 4 to 15.

The various fluorinated amines can be prepared using any known method. For example, the fluorinated amines can be prepared by forming or obtaining a compound of formula A-Rf-A. In this formula, group A refers to a carbonyl-containing group such as an alkoxycarbonyl or halocarbonyl. The preparation of such compounds is described, for example, in U.S. Pat. No. 3,250,807 (Fritz et al.) where an initiating fluorinated diacid such as perfluorosuccinyl fluoride is reacted with hexafluoropropylene oxide in bis(2-methoxyethyl) ether (i.e., diglyme) with a catalytic amount of potassium fluoride. This compound A-Rf-A can then be reacted with a diamine of formula R$^2$HN—Y$^3$—NHR$^2$ to prepare the fluorinated amines of Formula (VIc).

To prepare a compound of formula Rf—(CH$_2$OC$_3$H$_6$NH$_2$)$_2$, a compound of formula Rf—(COF)$_2$ can be reduced to Rf—(CH$_2$OH)$_2$. Acrylonitrile can then be added to the compound of formula Rf—(CH$_2$OH)$_2$ to give a compound of formula Rf—(CH$_2$OC$_2$H$_4$CN)$_2$. Rf—(CH$_2$OC$_2$H$_4$CN)$_2$ can then be reduced with hydrogen in the presence of ammonia and a platinum catalyst to form a compound of formula Rf—(CH$_2$OC$_3$H$_6$NH$_2$)$_2$.

To prepare a compound of formula Rf—(CH$_2$OC$_2$H$_4$NH$_2$)$_2$, a compound of formula Rf—(COF)$_2$ can be reduced to Rf—(CH$_2$OH)$_2$. The compound Rf—(CH$_2$OH)$_2$ can then be reacted with ethylene carbonate to form a compound of formula Rf—(CH$_2$OC$_2$H$_4$OH)$_2$. This compound can then be reacted with methanesulfonyl chloride to form a compound of formula Rf—(CH$_2$OC$_2$H$_4$OSO$_2$CH$_3$)$_2$. The compound Rf—(CH$_2$OC$_2$H$_4$OSO$_2$CH$_3$)$_2$ can be reacted with liquid ammonia to form Rf—(CH$_2$OC$_2$H$_4$NH$_2$)$_2$.

To prepare a compound of formula Rf—(C$_2$H$_4$NH$_2$)$_2$, a compound of formula Rf—(COF)$_2$ can be reacted with lithium iodide to form Rf—(I)$_2$. The compound Rf—(I)$_2$ can then be reacted with ethylene to form Rf—(C$_2$H$_4$I)$_2$. This product can be further reacted with liquid ammonia to form Rf—(C$_2$H$_4$NH$_2$)$_2$.

To prepare a compound of formula Rf—(CH$_2$NH$_2$)$_2$, a compound of formula Rf—(COF)$_2$ can be reacted with ammonia to form Rf—(CONH$_2$)$_2$ and then reduced with BH$_3$ to Rf—(CH$_2$NH$_2$)$_2$. An alternative synthesis method is described in Example XIV of U.S. Pat. No. 3,810,874 (Mitsch et al.).

An oxalate compound of Formula (I) is reacted with the fluorinated amine.

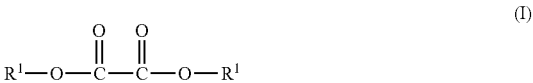
(I)

Each R$^1$ group in Formula (I) is independently an alkyl, haloalkyl, aralkyl, substituted aralkyl, alkenyl, aryl, substituted aryl, or imino of formula —N=CR$^4$R$^5$. The R$^4$ group is hydrogen, alkyl, aralkyl, substituted aralkyl, aryl, or substituted aryl. The R$^5$ group is alkyl, aralkyl, substituted aralkyl, aryl, or substituted aryl.

Suitable alkyl and haloalkyl groups for R$^1$ often have 1 to 10, 1 to 6, or 1 to 4 carbon atoms. Although tertiary alkyl (e.g., tert-butyl) and tertiary haloalkyl groups can be used, a primary or secondary carbon atom is often attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or fluoroalkyl groups can be 2-chloroethyl, 2,2,2-trichloroethyl, 3-chloropropyl, 4-chlorobutyl, fluoromethyl, 2-fluoroethyl, 2,2-difluoroethyl, 2,2,2-trifluoroethyl, 1-(trifluoromethyl)-2,2,2-trifluorethyl, 3-fluoropropyl, 4-fluorobutyl, and the like. Suitable alkenyl groups for R$^1$ often have 2 to 10, 2 to 8, 2 to 6, or 2 to 4 carbon atoms. Exemplary alkenyl groups include ethenyl, propenyl, butenyl, and pentenyl.

Suitable aryl groups for R$^1$ include those having 6 to 12 carbon atoms such as, for example, phenyl. The aryl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable aralkyl groups for R$^1$ include those having an alkyl group with 1 to 10 carbon atoms and an aryl group with 6 to 12 carbon atoms. For example, the aralkyl can be an alkyl having 1 to 10 carbon atoms or 1 to 4 carbon atoms substituted with phenyl. The aryl portion of the aralkyl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable imino groups for R$^1$ are monovalent groups of formula —N=CR$^4$R$^5$. Suitable alkyl groups for either R$^4$ or R$^5$ can be linear or branched and typically contain 1 to 10 carbon atoms, 1 to 8 carbon atoms, 1 to 6 carbon atoms, or 1 to 4 carbon atoms. Suitable aryl, substituted aryl, aralkyl, and substituted aralkyl groups for R$^4$ or R$^5$ are the same as those describe above for R$^1$.

The oxalate compound of Formula (I) can be prepared, for example, by reacting an alcohol of formula R$^1$—OH with oxalyl dichloride. Oxalates of Formula (I) are commercially available (e.g., from Sigma-Aldrich, Milwaukee, Wis. and from VWR International, Bristol, Conn.) and include, but are not limited to, dimethyl oxalate, diethyl oxalate, di-n-butyl oxalate, di-text-butyl oxalate, bis(phenyl) oxalate, bis(pentafluorophenyl) oxalate, 1-(2,6-difluorophenyl)-2-(2,3,4,5,6-pentachlorophenyl) oxalate, and bis(2,4,6-trichlorophenyl) oxalate.

The fluorinated amine (e.g., the fluorinated amine of Formula (V), (Va), (Vb), (Vc), (VI), (VIa), (VIb), (VIc), or (VId)) can be reacted with the oxalate compound of Formula (I). The reaction is a condensation reaction with the production of a by-product of formula R$^1$—OH (R'—OH can be an alcohol, phenol, or oxime). Any suitable ratio (based on equivalents) of the oxalate compound to the fluorinated amine can be used. The reaction product formed can be varied by altering this equivalents ratio.

If the ratio of equivalents (i.e., equivalents ratio) of the oxalate compound to equivalents of the fluorinated compound is greater than about 10, greater than about 15, or greater than about 20, the reaction product includes a compound of Formula (II).

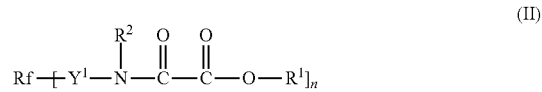

The groups Rf, Y$^1$, R$^1$, and R$^2$ as well as the variable n are the same as previously described. If the variable n is equal to 2, the product is of Formula (IIa).

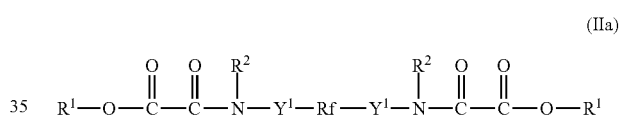

In some embodiments of Formula (II) or (IIa), each group Y$^1$ is equal to —Y$^2$—(CO)—NR$^2$—Y$^3$— and the compounds are of Formula (IIb) and (IIc), respectively.

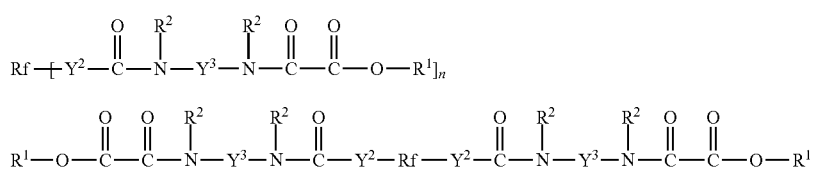

The groups Y$^2$ and Y$^3$ arc the same as previously described for Formula (VI).

If the ratio of equivalents of the oxalate compound to equivalents of the fluorinated compound is greater than about 2 and the fluorinated amine is of Formula (Vb), the product can be of Formula (III).

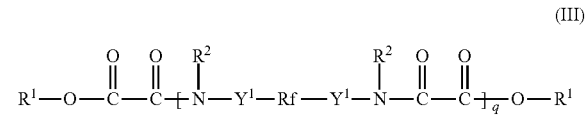

Groups Rf, R$^1$, R$^2$, and Y$^1$ are the same as previously described. The variable q is an integer equal to at least 1 and is often equal to at least 2, at least 3, or at least 5. The variable q is often no greater than 100, no greater than 50, no greater than 20, no greater than 15, or no greater than 10. The variable q is often in the range of 1 to 20, in the range of 2 to 20, in the range of 1 to 15, in the range of 1 to 10, in the range of 1 to 8, in the range of 1 to 6, in the range of 1 to 4, or in the range of 1 to 3. The value of q is affected by the ratio of the equivalents of the components reacted to form the compound of Formula (III).

The reaction product of Formula (III) often includes a mixture of materials having different values for the variable q. For example, at least 50 weight percent of the reaction product can has the variable q equal to 1 with the remainder of the reaction product having the variable q in the range of 2 to 20, in the range of 2 to 10, or in the range of 2 to 5. In some examples, at least 60 weight percent, at least 70 weight percent, at least 80 weight percent, at least 90 weight percent, at least 95 weight percent, or at least 98 weight percent of the reaction product has the variable q equal to 1 with the remainder of the reaction product having the variable q in the range of 2 to 20, in the range of 2 to 10, or in the range of 2 to 5.

If the ratio of equivalents of the oxalate compound to equivalents of the fluorinated amine is close to 1 and the fluorinated amine is of Formula (Vb), then a polymeric material can result. The polymeric material can be of Formula (IV).

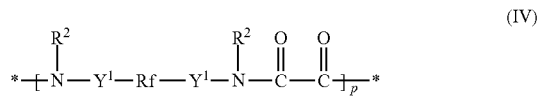

(IV)

In Formula (IV), groups $R^2$, $Y^1$, and Rf are the same as previously described. The variable p in an integer that is equal to at least 1. For example, variable p in an integer equal to at least 2, at least 3, at least 5, at least 10, at least 20, at least 30, at least 50, at least 100, at least 200, at least 500, or at least 1000. Each asterisk denotes a site of attachment to another group of the polymeric material. This other group can be, for example, another group of Formula (IV), an end group, or yet another segment in the copolymeric structure.

Polymeric material of Formula (IV) can also be formed by reacting a fluorinated oxalylamino-containing compound of Formula (IIa) or (III) with a fluorinated amine having a perfluoropolyether segment (e.g., the fluorinated amine of Formula (V), (Va), (Vb), (Vc), (VI), (VIa), (VIb), (VIc), (VId)). The fluorinated amine can be the same as or different than the compound used to form the fluorinated oxalylamino-containing compound. Alternatively, the polymeric material can be formed by reacting multiple different fluorinated amine compounds having perfluoropolyether segments with the oxalate compound of Formula (I) under the conditions used to form the polymeric material of Formula (IV).

Non-linear polymeric materials rather than linear polymeric material of Formula (IV) can be formed by reacting the oxalate compound with a fluorinated amine having more than two primary amino groups, more than two secondary amino groups, or more than one primary amino groups plus more than one secondary amino groups. The ratio of equivalents of the oxalate compound to equivalents of the fluorinated amine used to prepare these polymers is usually close to 1 such as, for example in the range of 0.9:1 to 1.1:1 or in the range of 0.8:1 to 1.2:1.

The condensation reaction between the oxalate compound and the fluorinated amine to produce a compound of Formula (II), (III), or (IV) can occur in the presence or in the absence of a solvent. In some synthesis methods, no solvent or only a small amount of solvent is included in the reaction mixture. The absence of a solvent can be desirable when the removal of the solvent would be advantageous for the subsequent use of the product of the condensation reaction. In other synthesis methods, a solvent may included such as, for example, toluene, tetrahydrofuran, dichloromethane, ethyl acetate, trifluoroethanol, trifluorotoluene, tert-butyl methyl ether, hexafluoroisopropanol, or aliphatic hydrocarbons (e.g., alkanes such as hexane).

Any excess oxalate compound can typically be removed from the desired reaction product of the condensation reaction (i.e., from the compounds of Formulas (II), (III), or (IV)) using a stripping process. For example, the reacted mixture (i.e., the product or products of the condensation reaction) can be heated to a temperature up to 150° C., up to 175° C., up to 200° C., up to 225° C., or up to 250° C. or even higher to volatilize the excess oxalate. Application of a vacuum can lower the temperature that is needed for removal of the excess oxalate. The compounds of Formula (II), (III), or (IV) typically undergo minimal or no apparent degradation at temperatures up to 250° C. Any other known methods for removing the oxalate can be used.

The by-product of the condensation reaction is of formula $R^1$—OH where $R^1$—OH is an alcohol, a phenol, or an oxime. Group $R^1$ is often selected to produce a by-product that can be removed (e.g., vaporized) by heating at temperatures no greater than about 250° C. Such a by-product can be removed when the reacted mixture is heated to remove any excess oxalate compound.

The polymeric material of Formula (IV) has both oxalylamino groups and perfluoropolyether segments. The oxalylamino groups are capable of hydrogen bonding. Hydrogen bonding tends to increase the strength and rigidity of the polymeric material. Unlike many known perfluoropolyether materials that are soft and tacky, the polymeric material of Formula (IV) can be used to provide durable coatings. The polymeric materials retain many of the desirable characteristics normally associated with perfluoropolyether materials such as low surface energy, oil and/or water repellency, and low refractive index.

The compounds of Formulas (II) and (III) can be used as fluorinated precursors for the preparation of various copolymeric materials having perfluoropolyether segments. For example, these fluorinated oxalylamino-containing precursors can be reacted with other amine compounds. More specifically, the compounds of Formula (II) and (III) can undergo a condensation reaction with an amine compound having at least two primary amino groups, at least two secondary amino groups, or at least one secondary amino group plus at least one primary amino group to form various copolymers having a plurality of aminooxalylamino groups and at least one perfluoropolyether segment. These polymeric materials can be used, for example, in applications where low surface energy materials or low refractive index materials are desired.

The resulting copolymeric materials have increased hydrogen bonding compared to many perfluoropolyether materials. This increased hydrogen bonding can give additional strength and rigidity to the copolymeric material. These copolymeric materials can be used, for example, in applications where abrasion resistance is desired. The amine compound that is reacted with the compounds of Formula (II) or (III) can be used to modify the properties of perfluoropolyether materials while maintaining the characteristics of the perfluoropolyether materials such as oil and/or water repellency.

Various items are provided including various products of reaction mixtures, compounds, and polymers.

A first item is provided that includes a product of a reaction mixture. The reaction mixture includes a) a fluorinated amine having a perfluoropolyether segment and having at least two primary amino groups, at least two secondary amino groups, or at least one primary amino group plus at least one secondary amino group and b) an oxalate compound of Formula (I).

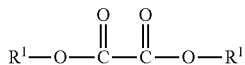
(I)

In Formula (I), each $R^1$ is independently an alkyl, haloalkyl, aralkyl, substituted aralkyl, alkenyl, aryl, substituted aryl, or imino of formula $-N=CR^4R^5$. Group $R^4$ is hydrogen, alkyl, aralkyl, substituted aralkyl, aryl, or substituted aryl. Group $R^5$ group is analkyl, aralkyl, substituted aralkyl, aryl, or substituted aryl.

A second item is provided that can be a version of the first item. In the second item, the fluorinated amine is a compound of Formula (V).

$$Rf\mathrm{-\!\!\!-\!\!\![}Y^1\mathrm{-\!\!\!-\!\!\!NHR^2}\mathrm{-\!\!\!-\!\!\!]}_n \qquad (V)$$

In Formula (V), Rf is a perfluoropolyether group. Each $R^2$ is independently hydrogen, alkyl, aryl, or aralkyl. Each $Y^1$ is independently (a) a heteroalkylene, (b) alkylene, (c) a carbonylamino group linking a first group to a second group, wherein the first group and the second group are each a heteroalkylene or alkylene, or (d) a combination thereof. The variable n is an integer equal to at least 2.

A third item is provided that can be a version of the first item or the second item. In the third item, the fluorinated amine is of Formula (Vb).

$$R^2HN\mathrm{-\!\!\!-}Y^1\mathrm{-\!\!\!-}Rf\mathrm{-\!\!\!-}Y^1\mathrm{-\!\!\!-}NHR^2 \qquad (Vb)$$

A fourth item is provided that can be a version of any one of the first to third items. In the fourth item, the fluorinated amine is $Rf-(CH_2CH_2NH_2)_2$, $Rf-(CH_2NH_2)_2$, $Rf-(CH_2OC_3H_6NH_2)_2$, $Rf-(CH_2OC_2H_4NH_2)_2$, or a mixture thereof.

A fifth item is provided that can be a version of the first or second items. In the fifth item, the fluorinated amine is of Formula (VI)

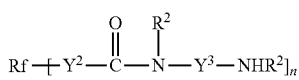
(VI)

Group $Y^1$ in Formula (V) is equal to $-Y^2-(CO)-NR^2-Y^3-$ in Formula (VI). In Formula (VI), each $Y^2$ is independently a single bond, heteroalkylene, alkylene, or combination thereof; and each $Y^3$ is independently a heteroalkylene, alkylene, or combination thereof.

A sixth item is provided that can be a version of the first to fifth items. In the sixth item, Rf is of the following formula $-CF(CF_3)[OCF_2CF(CF_3)]_bOCF_2-R^6-CF_2O[CF(CF_3)CF_2O]_dCF(CF_3)$. In this formula, the group $R^6$ is a perfluoroalkylene group having 1 to 20 carbon atoms; and the variables b and d are both integers with a sum in the range of 0 to 35.

A seventh item is provided that can be a version of the fifth item. In the seventh item, n is equal to 2 and the fluorinated amine is a compound of Formula (VIa).

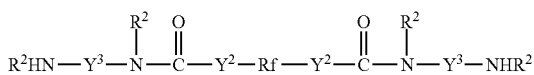
(VIa)

An eight item is provided that is a compound of Formula (II).

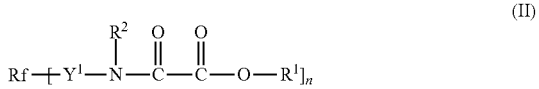
(II)

In Formula (II), Rf is a perfluoropolyether group. Each $Y^1$ is independently (a) a heteroalkylene, (b) alkylene, or (c) a carbonylamino group linking a first group to a second group, wherein the first group and the second group are each a heteroalkylene or alkylene, or (d) a combination thereof. Each $R^1$ is independently an alkyl, haloalkyl, aralkyl, substituted aralkyl, alkenyl, aryl, substituted aryl, or imino of formula $-N=CF^4R^5$. Each $R^2$ is independently hydrogen, alkyl, aralkyl, or awl. The group $R^4$ is a hydrogen, alkyl, aralkyl, substituted aralkyl, aryl, or substituted aryl; and the group $R^5$ is an alkyl, aralkyl, aryl, or substituted aryl. The variable n is an integer equal to at least 2.

A ninth item is provided that can be a version of the eighth item. In the ninth item, the variable n is equal to 2 and the compound is of Formula (IIa).

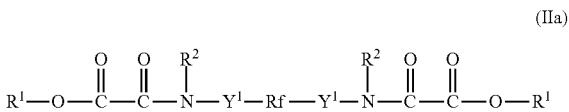
(IIa)

A tenth item is provided that can be a version of the eighth item. In the tenth item, the compound is of Formula (IIb).

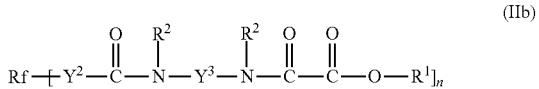
(IIb)

The group $Y^1$ in Formula (II) is equal to $-Y^2-(CO)-NR^2-Y^3-$ in Formula (IIb). Each $Y^2$ is independently a single bond, heteroalkylene, alkylene, or combination thereof. Each $Y^3$ is independently a heteroalkylene, alkylene, or combination thereof.

An eleventh item is provided that can be a version of the tenth item. In the eleventh item, the variable n is equal to 2 and the compound is of Formula (IIc).

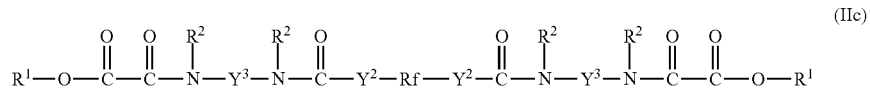
(IIc)

A twelfth item is provided that can be a version of the eighth to eleventh items. The group Rf is of formula —CF(CF$_3$)[OCF$_2$CF(CF$_3$)]$_b$OCF$_2$—R$^6$—CF$_2$O[CF(CF$_3$)CF$_2$O]$_d$CF(CF$_3$)—. The group R$^6$ is a perfluoroalkylene group having 1 to 20 carbon atoms. The variables b and d are both integers with a sum in the range of 0 to 35.

A thirteenth item is provided that is a compound of Formula (III).

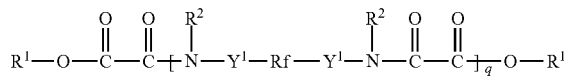

In Formula (III), Rf is a perfluoropolyether group. Each Y$^1$ is independently (a) a heteroalkylene, (b) alkylene, (c) a carbonylamino group linking a first group to a second group, wherein the first group and the second group are each a heteroalkylene or alkylene, or (d) a combination thereof. Each R$^1$ is independently an alkyl, haloalkyl, aralkyl, substituted aralkyl, alkenyl, aryl, substituted aryl, or imino of formula —N=CR$^4$R$^5$. Each R$^2$ is independently hydrogen, alkyl, aralkyl, or aryl. Group R$^4$ group is hydrogen, alkyl, aralkyl, substituted aralkyl, aryl, or substituted awl. Group R$^5$ group is alkyl, aralkyl, substituted aralkyl, aryl, or substituted awl. The variable q is an integer equal to at least 1.

A fourteenth item is provided that can be a version of the thirteenth item. In the fourteenth item, each Y$^1$ is equal to a group of formula —Y$^2$—(CO)—NR$^2$—Y$^3$—. Each Y$^2$ is independently a single bond, heteroalkylene, alkylene, or combination thereof; and each Y$^3$ is independently a heteroalkylene, alkylene, or combination thereof.

A fifteenth item is provided that can be a version of the thirteenth or fourteenth items. In the fifteenth item, the group Rf is of formula —CF(CF$_3$)[OCF$_2$CF(CF$_3$)]$_b$OCF$_2$—R$^6$—CF$_2$O[CF(CF$_3$)CF$_2$O]$_d$CF(CF$_3$)—. In this formula, group R$^6$ is a perfluoroalkylene group having 1 to 20 carbon atoms; and b and d are both integers with a sum in the range of 0 to 35.

A sixteenth item is provided that is a polymeric material that includes at least one group of Formula (IV).

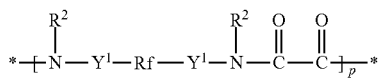

In Formula (IV), Rf is a perfluoropolyether group. Each Y$^1$ is independently (a) a heteroalkylene, (b) alkylene, or (c) a carbonylamino group linking a first group to a second group, wherein the first group and the second group arc each a heteroalkylene or alkylene, or (d) a combination thereof. Each R$^2$ group is independently hydrogen, alkyl, aryl, or aralkyl. The variable p is an integer equal to at least 1. Each asterisk denotes a site of attachment to another group of the polymeric material.

A seventeenth item is provided that can be a version of the sixteenth item. In the seventeenth item, each Y$^1$ is equal to a group of formula —Y$^2$—(CO)—NR$^2$—Y$^3$—. Each Y$^2$ is independently a single bond, heteroalkylene, alkylene, or combination thereof; and each Y$^3$ is independently a heteroalkylene, alkylene, or combination thereof.

An eighteenth item is provided that can be a version of the sixteenth or seventeenth item. In the eighteenth item, Rf is of formula —CF(CF$_3$)[OCF$_2$CF(CF$_3$)]$_b$OCF$_2$—R$^6$—CF$_2$O[CF(CF$_3$)CF$_2$O]$_d$CF(CF$_3$)—. The group R$^6$ is a perfluoroalkylene group having 1 to 20 carbon atoms. The variables b and d are both integers with a sum in the range of 0 to 35.

EXAMPLES

These examples are for illustrative purposes only and are not meant to be limiting on the scope of the appended claims. All parts, percentages, and ratios in the examples are by weight unless otherwise noted. Solvents and other reagents used can be obtained from Sigma-Aldrich Chemical Company (Milwaukee, Wis.) unless otherwise noted.

Materials

As used herein, the term "HFPO" refers to monovalent or divalent poly(hexafluoropropylene oxide) segment. In some embodiments the HFPO segment is a monovalent group of formula F(CF(CF$_3$)CF$_2$O)$_a$CF(CF$_3$)— where the variable a is an integer in the range of about 4 to about 20 or is a divalent group of formula —CF(CF$_3$)(OCF$_2$CF(CF$_3$)$_b$OCF$_2$CF$_2$CF$_2$CF$_2$O(CF(CF$_3$)CF$_2$O)$_d$CF(CF$_3$)— where the sum (b+d) is an integer in the range of about 4 to about 15.

Preparatory Example 1

Synthesis of H$_3$CO(CO)—HFPO—(CO)OCH$_3$—Method 1

A dimethyl ester of poly(hexafluoropropylene oxide) was prepared using F(CO)CF$_2$CF$_2$(CO)F as an starting material according to the method reported in U.S. Pat. No. 3,250,807 (Fritz, et al.) which provides the HFPO oligomer bis-acid fluoride. The HFPO oligomer bis-acid fluoride was subjected to methanolysis and purification by removal of lower boiling materials by fractional distillation as described in U.S. Pat. No. 6,923,921 (Flynn, et. al.). The resulting material was of formula H$_3$CO(CO)CF(CF$_3$)(OCF$_2$CF(CF$_3$)$_b$OCF$_2$CF$_2$CF$_2$O(CF(CF$_3$)CF$_2$O)$_d$CF(CF$_3$)(CO)OCH$_3$ where the sum (b+d) is an integer in the range of about 4 to about 15. This formula is also be referred to interchangeably as H$_3$CO(CO)—HFPO—(CO)OCH$_3$ or HFPO—((CO)OCH$_3$)$_2$ or HFPO dimethyl ester or HFPO-DME.

More specifically, a 600-mL jacketed reactor, which is commercially available under the trade designation PARR from Parr Instrument Company (Moline, Ill.), was charged with KF (15.1 grams, 0.26 moles) and tetraglyme (125 grams). The reactor was stirred, evacuated to 0.033 atmosphere vacuum using a vacuum pump and cooled to 4° C. A charge of of perfluorosuccinyl fluoride (85 grams, 0.44 moles) that was obtained from Exfluor Research Corporation (Austin, Tex.) was added to the reactor. External cooling was used to cool the contents of the reactor to 0° C. before adding hexafluoropropylene oxide (482 grams, 2.9 moles) slowly over 5 hours. The hexafluoropropylene oxide was obtained from DuPont (Wilmington, Del.). The maximum pressure was 2.38 atmospheres and an exotherm of 8° C. resulted. After addition was completed, the reactor was warmed to room temperature and nitrogen was used to break the 0.033 atmosphere reactor vacuum and to increase the pressure within the reactor to atmospheric pressure.

The crude mixture of 690 grams was drained from the reactor and reacted with methanol (120 grams, 3.8 moles) to convert the diacid fluoride ends to dimethyl ester end groups. The fluorochemical crude product was isolated by adding a fluorinated solvent (300 grams), which is commercially available under the trade designation FC77 FLUORINERT form 3M Company (Saint Paul, Minn.), and by water washing twice. The lower fluorochemical phase was stripped of fluorinated solvent and the product was isolated by taking a cut that boiled from 130-190° C. The yield was 390 grams (71 percent) of HFPO dimethyl ester having a number average molecular weight of 1250 grams/mole and 96 percent functionality determined by NMR end group analysis.

Preparatory Example 2

Synthesis of $H_3CO(CO)$—HFPO—$(CO)OCH_3$—Method 2

A dimethyl ester of poly(hexafluoropropylene oxide) was prepared from the oligomerization reaction of hexafluoropropylene oxide (5900 grams, 35.5 moles) in the presence of perfluorosuccinyl fluoride (511 grams, 2.6 moles) and KF (102 grams, 1.75 moles) in tetraglyme (1008 grams) at 5° C. in essentially the same manner as described in Preparatory Example 1. The hexafluoropropylene oxide was added at a rate of 1500 grams/hour. After the oligomerization reaction was completed, methanol was added and HFPO dimethyl ester was vacuum distilled for a yield of 80 percent. The molecular weight was 2400 grams/mole.

Preparatory Example 3

Synthesis of $CH_3O(CO)CH_2OCH_2$—HFPO—$CH_2OCH_2(CO)_3$

HFPO dimethyl ester (HFPO—$((CO)OCH_3)_2$)) was prepared using the procedure of Preparatory Example 1. Vacuum distillation of low boiling monofunctionals was done to bring the difunctionality to greater than 99 percent. The average molecular weight was determined as 1534 grams/mole using fluorine nuclear magnetic resonance (FNMR) spectroscopy end group analysis. Reaction with methanol gave the dimethyl ester after water washing out HF and vacuum drying to remove water.

The HFPO dimethyl ester was reduced to HFPO diol (HFPO—$(CH_2OH)_2$) using the following procedure. Sodium borohydride ($NaBH_4$, 44 grams, 1.16 mol) and dimethoxy ethane (620 grams), which is also known as glyme, were added to a 5 liter three-neck reaction flask having a round bottom. Both the $NaBH_4$ and the glyme were obtained from Aldrich Chemical Company (Milwaukee, Wis.). The HFPO dimethyl ester (605 grams, 0.40 mol) was dissolved in a fluorinated solvent (400 grams) commercially available from 3M Company (Saint Paul, Minn.) under the trade designation FC77 FLUORINERT. This solution was slowly added to the reaction flask at room temperature. A slight exotherm resulted. After complete addition of the solution, the reaction mixture was stirred for one hour and then the reaction was quenched with a sulfuric acid solution prepared by diluting concentrated sulfuric acid (125 grams, 1.28 mol) with water (1000 grams). The fluorochemical bottom phase was collected. The fluorinated solvent was removed by vacuum distillation (110 to 200° C. with 0.1 millimeter vacuum). The yield of the HFPO diol (496 grams) was 85 percent.

Into a 500-mL 3-neck round bottom flask were added HFPO diol (245 grams, 0.17 mol) with a molecular weight of 1458 grams/mole, NaH that was 60 weight percent in mineral oil (15 grams, 0.38 mol), and tetrahydrofuran (THF) solvent (400 grams). The mixture in the flask was mechanically stirred. Over a period of 30 minutes, $BrCH_2(CO)OCH_3$ (70 grams, 0.45 mole) was added giving a slight exotherm. The temperature was held at 80° C. for 2 hours. The product mixture was vacuum distilled and washed with hexane and the fluorinated solvent commercially available under the trade designation FC77 FLUORINERT from 3M Company (St. Paul, Minn.) to remove the mineral oil from the top organic phase. Final vacuum distillation gave 210 grams (0.13 moles) of the chain extended diester ($CH_3O(CO)CH_2OCH_2]_2$)—HFPO) with a molecular weight of 1600 grams/mole and having a boiling point of 195° C./3 mm. The yield was 78 percent.

Preparatory Example 4

Synthesis of $H_2NCH_2CH_2$—NH(CO)—HFPO—(CO)NH—$CH_2CH_2NH_2$—Method 1

A 1 L 3-necked round bottom flask that was equipped with a magnetic stir bar, $N_2$ inlet and reflux condenser was charged with $NH_2$—$CH_2CH_2$—$NH_2$ (420.0 grams, 7 moles) under $N_2$ atmosphere. The charge was heated to 75° C. Then the HFPO—$[COOMe]_2$ (150.0 grams, 8.75×10$^{-2}$ moles) of Preparatory Example 1 was added dropwise at 75° C. over a period of 180 minutes. The reaction mixture was stirred under $N_2$ atmosphere for 12 hours and the progress of the reaction was monitored by IR spectroscopy. After the disappearance of the ester peak at 1792 cm$^{-1}$ and appearance of the NH—C=O peak at 1719 cm$^{-1}$, the reaction mixture was poured onto a separation funnel and the lower portion was collected in a flask and dried under high vacuum for another 8 hours. The viscous oil obtained was used as such.

Preparatory Example 5

Synthesis of $H_2NCH_2CH_2$—NH(CO)—HFPO—(CO)NH—$CH_2CH_2NH_2$—Method 2

A 100-mL flask was charged with HFPO dimethyl ester of Preparatory Example 2 (2400 grams/mole, 0.04 moles, 96 grams) and ethylene diamine (0.8 mole, 48 grams). The heterogeneous solution was stirred, heated to 50° C., and held at 50° C. for 1 hour. Then the solution was heated to 90° C. and the unreacted ethylene diamine was distilled out of the flask under 0.0013 atmospheres. Infrared spectroscopy confirmed complete conversion by the disappearance of the ester at 1760 cm$^{-1}$ and appearance of the amide at 1666 cm$^{-1}$. The desired product was produced as a viscous liquid.

Preparatory Example 6

Synthesis of $H_2NCH_2CH_2NH(CO)CH_2OCH_2$—HFPO—$CH_2OCH_2(CO)NHCH_2CH_2NH_2$

The HFPO diester of Preparatory Example 3 (1600 grams/mole, 0.02 moles, 32 grams) was combined with ethylene diamine (0.2 mole, 12 grams). The heterogeneous solution was stirred, heated to 50° C., and held at 50° C. for 1 hour. Then the solution was heated to 90° C. and the unreacted ethylene diamine was distilled out of the flask under 0.0013 atmospheres. Infrared spectroscopy confirmed complete conversion by the disappearance of the ester at 1760 cm$^{-1}$ and appearance of the amide at 1666 cm$^{-1}$.

Preparatory Example 7

Synthesis of H$_2$N[CH$_2$CH$_2$O]$_2$CH$_2$CH$_2$NH(CO)—HFPO—(CO)NHCH$_2$CH$_2$[OCH$_2$CH$_2$]$_2$NH$_2$ A 1000-mL, 3-necked round bottom flask was equipped with a magnetic stir bar, N$_2$ inlet and reflux condenser. The flask was charged with (52.9 grams, 0.3 moles) NH$_2$CH$_2$CH$_2$—O—CH$_2$CH$_2$—O—CH$_2$CH$_2$NH$_2$ (triethyleneglycol diamine—TEGDA) under N$_2$ atmosphere. The charge was heated to 75° C. The HFPO-DME of Preparatory Example 1 (5.0 grams, 3.75×10$^{-2}$ moles) was added dropwise to this solution at 75° C. over a period of 180 minutes. The reaction mixture was stirred under N$_2$ atmosphere for 12 hours and was monitored by IR. After the disappearance of ester peak, the reaction mixture was poured onto a separation funnel and the lower portion was collected in a flask and dried under high vacuum for another 8 hours. The viscous oil obtained was used as such.

Preparatory Example 8

Synthesis of Di(methylethylketoxime)oxalate

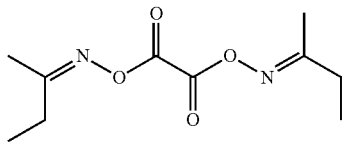 [SMILES: CC/C(C)=N\OC(=O)C(=O)O/N=C(\C)CC]

To a 1 L flask equipped with an overhead stirrer, addition funnel, ice bath, temperature probe, and nitrogen inlet was added 2-butanone oxime (93.23 grams, 1.070 moles) and butyl methyl ether (500 mL). The contents were cooled to 10° C., and oxalyl chloride (67.9 grams, 0.535 moles) was added over 30 minutes while maintaining the internal temperature below 15° C. Triethylamine (108 grams, 1.07 moles) was then added dropwise over 30 minutes with external cooling to maintain the internal temperature below 30° C. Enough water was added to dissolve the resulting solids, and then the aqueous layer was drawn off. The organic layer was washed twice with 0.1N HCl and once with 2M sodium carbonate, after which it was dried over MgSO$_4$ and filtered through a pad of Celite. The solvent was removed on a rotary evaporator to afford 120 grams of di(methyl ethyl ketoxime) oxalate as a clear, colorless oil. $^1$H NMR (CDCl$_3$) was consistent with the proposed structure. The material was present as a mixture of stereoisomers.

Example 1

Into a 250-mL 3-necked flask was weighed dry diethyl oxalate (DEO) (87.7 grams, 1.20 equivalents). The flask was fitted with a stirrer and a gentle argon sweep of the flask was started. With vigorous stirring of the DEO, the fluorinated diamine of Preparatory Example 4 (60.0 grams (3.27×10$^{-2}$ equivalents) was added dropwise from an addition funnel over about a period of 75 minutes. After all of the fluorinated diamine was added, the addition funnel was removed and the flask was set up for distillation. Under high vacuum of 0.0013 atmospheres, the temperature was slowly increased from ambient to 165° C. The excess DEO and ethanol formed during the reaction were distilled out of the flask. About 65 grams (approximately 94.5 percent of the theoretical yield) of the oxalylamino ester terminated product was isolated. Back titration with ethanolamine and 1N HCl showed that the ester had an equivalent weight of 1,006 grams/equivalent.

Example 2

Into a 250-mL 3-necked flask was weighed dry DEO (64.9 grams). The flask was fitted with a stirrer and a gentle argon sweep of the flask was started. With vigorous stirring of the DEO, the fluorinated amine of Preparatory Example 7 (150.0 grams) was added dropwise from an addition funnel over about a period of 120 minutes. After all of the fluorinated amine was added, the additional funnel was removed and the flask was set up for distillation. Under high vacuum, the temperature was slowly increased from ambient to 165° C. The excess DEO and ethanol formed during the reaction were distilled out of the flask. About 147.38 grams (94.2 percent of the theoretical yield) of the oxalylamino ester terminated precursor product was isolated. Back titration of the product with ethanolamine and 1N HCl showed an ester equivalent weight of 1,950 grams/equivalent.

Example 3

A HFPO diester was prepared in a manner similar to that described for Preparatory Example 2. The number average molecular weight was 3000 grams/mole. A 50-mL flask was charged with HFPO diester (0.01 moles, 30 grams) and ethylene diamine (0.2 moles, 12 grams). The heterogeneous solution was stirred and heated to 60° C. for 1 hour. Then the solution was heated to 90° C. and the unreacted ethylene diamine was distilled out of the flask under 0.0013 atmospheres. Then, diethyl oxalate (0.01 moles, 1.46 grams) was added to the flask. The solution was slowly heated from room temperature to 150° C. within 1 hour and then kept at 150° C. for 2 hours. The viscous solution was poured into glass plate and kept at 200° C. for 2 hours. A brown film was prepared that was flexible and tough. The refractive index of the polymer was 1.3323.

Example 4

A 100-mL flask was charged with HFPO diester of Preparatory Example 2 (2400 grams/mole, 0.02 moles, 48 grams) and ethylene diamine (0.4 moles, 24 grams). The heterogeneous solution was stirred and heated to 50° C. for 1 hour. Then the solution was heated to 90° C. and the unreacted ethylene diamine was distilled out of the flask under 0.0013 atmospheres. Then, diethyl oxalate (0.02 moles, 2.92 grams) was added to the flask. The solution was slowly heated from room temperature to 100° C. within 1 hour and then kept at 100° C. for 1 hour. The viscous solution was poured into glass plate and kept at 200° C. for 2 hours. A brown film was prepared that was flexible and tough. The polymer had a melting temperature of 96° C. and initial decomposition temperature of 360.3° C.

Example 5

A 100-mL flask was charged with the fluorinated diamine of Preparatory Example 6 (1658 grams/mole, 0.005 mole, 8.29 grams) and diethyl oxalate (0.005 moles, 0.73 grams). The solution was slowly heated from room temperature to 150° C. within 1 hour and then kept at 150° C. for 10 hours. A brown solid polymer was prepared.

Example 6

In a vial, the fluorinated amine of Preparatory Example 4 (1.0876 grams, 1.19×10$^{-3}$ equivalents) was dissolved in anhydrous THF (10.0 grams). Then di(methyl ethyl ketoxime) oxalate (0.1352 grams, 1.19×10$^{-3}$ equivalents) of Preparatory Example 8 was added and mixed on a roller for one day under ambient lab conditions. The resulting polymer formed a gel that precipitated from the solution. The reaction mixture was mixed for about 65 hours in a Launder-O-Meter (available from Atlas Electric Devices Co., Chicago, Ill.) at 50° C. and then on a roller for one day under ambient lab conditions. The polymer was dried in an aluminum weighing dish in a fume hood and then overnight at 60° C. The polymer obtained was a clear, colorless plastic with a refractive index of 1.3509.

Example 7

In a vial, the fluorinated amine of Preparatory Example 7 (1.0371 grams, 8.53×10$^{-4}$ equivalents) was dissolved in anhydrous THF (10.0 grams). Then di(methyl ethyl ketoxime) oxalate of Preparatory Example 8 (0.0973 grams, 8.53×10$^{-4}$ equivalents) was added. The reaction mixture was mixed for about 65 hours in a Launder-O-Meter (available from Atlas Electric Devices Co., Chicago, Ill.) at 50° C. and then on a roller for one day under ambient lab conditions. The polymer was dried in an aluminum weighing dish in a fume hood and then overnight at 60° C. The polymer obtained was an elastomer.

Example 8

In a vial, the fluorinated amine of Preparatory Example 4 (0.9953 grams, 1.08×10$^{-3}$ equivalents) was dissolved in anhydrous THF (10.1 grams). Diphenyl oxalate (0.1313 grams, 1.08×10$^{-3}$ equivalents) that was obtained from TCI America (Portland, Oreg.) was added. The reaction mixture was mixed on a roller for one day under ambient lab conditions. The polymer formed a gel that precipitated from solution. The reaction mixture was mixed for about 65 hours in a Launder-O-Meter (available from Atlas Electric Devices Co., Chicago, Ill.) at 50° C. and then on a roller for one day under ambient lab conditions. The polymer was dried in an aluminum weighing dish in a fume hood and then overnight at 60° C. The polymer obtained was a clear, colorless plastic with a refractive index of 1.3509.

Example 9

In a vial, the fluorinated amine of Preparatory Example 7 (1.1055 grams, 9.09×10$^{-4}$ equivalents) was dissolved in anhydrous THF (9.15 grams). Diphenyl oxalate (0.1096 grams, 9.09×10$^{-4}$ equivalents) was added and mixed on a roller for one day under ambient lab conditions. The reaction mixture then was mixed over 48 hours in a Launder-O-Meter at 50° C. and then on a roller for one day under ambient lab conditions. The polymer was dried in an aluminum weighing dish in a fume hood and then overnight at 60° C. The polymer obtained was an elastomer.

Example 10

In a glass vial, the fluorinated oxalylamino-containing compound of Example 1 (4.8032 grams, 4.77×10$^{-3}$ equivalents) was dissolved in hexafluoroisopropanol (20.23 grams). A fluorinated diamine (4.3835 grams, 4.77$^{-3}$ equivalents) that was prepared as described in Preparatory Example 4 was added via a Gastight syringe. The reaction mixture was mixed overnight in a Launder-O-Meter at 55° C. and then on a roller over the weekend under ambient lab conditions. The polymer was dried in an aluminum weighing dish in a fume hood and then overnight at 60° C. The polymer obtained was a clear elastomer.

We claim:

1. A compound of Formula (II)

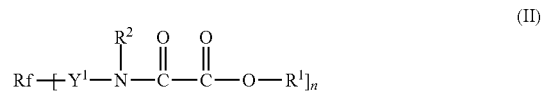

(II)

wherein
Rf is a perfluoropolyether group;
each Y$^1$ is independently (a) a heteroalkylene, (b) alkylene, or (c) a carbonylamino group linking a first group to a second group, wherein the first group and the second group are each a heteroalkylene or alkylene, or (d) a combination thereof;
each R$^1$ is independently an alkyl, haloalkyl, aralkyl, substituted aralkyl, alkenyl, aryl, substituted aryl, or imino of formula —N=CR$^4$R$^5$;
each R$^2$ is independently hydrogen, alkyl, aralkyl, or aryl;
R$^4$ is a hydrogen, alkyl, aralkyl, substituted aralkyl, aryl, or substituted aryl; and
R$^5$ is an alkyl, aralkyl, aryl, or substituted aryl; and
n is an integer equal to at least 2.

2. The compound of claim 1, wherein n is equal to 2 and the compound is of Formula (IIa).

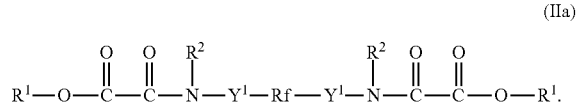

(IIa)

3. The compound of claim 1, wherein the compound is of Formula (IIb)

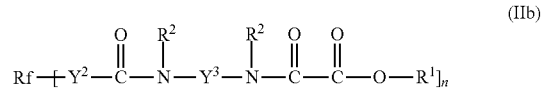

(IIb)

wherein
Y$^1$ in Formula (II) is equal to —Y$^2$—(CO)—NR$^2$—Y$^3$— in Formula (IIb);
each Y$^2$ is independently a single bond, heteroalkylene, alkylene, or combination thereof and
each Y$^3$ is independently a heteroalkylene, alkylene, or combination thereof.

4. The compound of claim 3, wherein n is equal to 2 and the compound is of Formula (IIc).

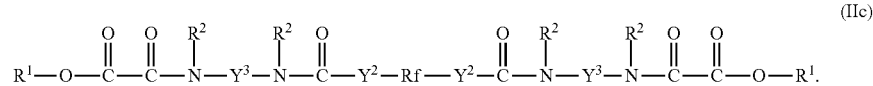

(IIc)

5. The compound of claim 1, wherein Rf is of formula $$-CF(CF_3)[OCF_2CF(CF_3)]_bOCF_2-R^6-CF_2O[CF(CF_3)CF_2O]_dCF(CF_3)-$$

wherein
 $R^6$ is a perfluoroalkylene group having 1 to 20 carbon atoms; and
 b and d are both integers with a sum in the range of 0 to 35.

6. A compound of Formula (III)

$$R^1-O-\overset{O}{\underset{\|}{C}}-\overset{O}{\underset{\|}{C}}+\overset{R^2}{\underset{|}{N}}-Y^1-Rf-Y^1-\overset{R^2}{\underset{|}{N}}-\overset{O}{\underset{\|}{C}}-\overset{O}{\underset{\|}{C}}\overset{}{\underset{q}{\Big)}}O-R^1 \quad (III)$$

wherein
 Rf is a perfluoropolyether group;
 each $Y^1$ is independently (a) a heteroalkylene, (b) alkylene, (c) a carbonylamino group linking a first group to a second group, wherein the first group and the second group are each a heteroalkylene or alkylene, or (d) a combination thereof
 each $R^1$ is independently an alkyl, haloalkyl, aralkyl, substituted aralkyl, alkenyl, aryl, substituted aryl, or imino of formula $-N=CR^4R^5$;
 each $R^2$ is independently hydrogen, alkyl, aralkyl, or aryl;
 $R^4$ is hydrogen, alkyl, aralkyl, substituted aralkyl, aryl, or substituted aryl;
 $R^5$ is alkyl, aralkyl, substituted aralkyl, aryl, or substituted aryl; and
 q is an integer equal to at least 1.

7. The compound of claim 6, wherein each $Y^1$ is equal to a group of formula $$Y^2-(CO)-NR^2-Y^3-$$

wherein
 each $Y^2$ is independently a single bond, heteroalkylene, alkylene, or combination thereof; and
 each $Y^3$ is independently a heteroalkylene, alkylene, or combination thereof.

8. The compound of claim 6, wherein Rf is of formula $$-CF(CF_3)[OCF_2CF(CF_3)]_bOCF_2-R^6-CF_2O[CF(CF_3)CF_2O]_dCF(CF_3)-$$

wherein
 $R^6$ is a perfluoroalkylene group having 1 to 20 carbon atoms; and
 b and d are both integers with a sum in the range of 0 to 35.

9. A polymeric material comprising at least one group of Formula (IV)

$$*+\overset{R^2}{\underset{|}{N}}-Y^1-Rf-Y^1-\overset{R^2}{\underset{|}{N}}-\overset{O}{\underset{\|}{C}}-\overset{O}{\underset{\|}{C}}\overset{}{\underset{p}{\Big)}}* \quad (IV)$$

wherein
 Rf is a perfluoropolyether group;
 each $Y^1$ is independently (a) a heteroalkylene, (b) alkylene, or (c) a carbonylamino group linking a first group to a second group, wherein the first group and the second group are each a heteroalkylene or alkylene, or (d) a combination thereof
 each $R^2$ is independently hydrogen, alkyl, aryl, or aralkyl;
 p is an integer equal to at least 1; and
 each asterisk denotes a site of attachment to another group of the polymeric material.

10. The polymeric material of claim 9, wherein each $Y^1$ is equal to a group of formula $-Y^2-(CO)-NR^2-Y^3-$,
 wherein
 each $Y^2$ is independently a single bond, heteroalkylene, alkylene, or combination thereof and
 each $Y^3$ is independently a heteroalkylene, alkylene, or combination thereof.

11. The polymeric material of claim 9, wherein Rf is of formula $$-CF(CF_3)[OCF_2CF(CF_3)]_bOCF_2-R^6-CF_2O[CF(CF_3)CF_2O]_dCF(CF_3)-$$

wherein
 $R^6$ is a perfluoroalkylene group having 1 to 20 carbon atoms; and
 b and d are both integers with a sum in the range of 0 to 35.

* * * * *

UNITED STATES PATENT AND TRADEMARK OFFICE
CERTIFICATE OF CORRECTION

PATENT NO. : 8,907,120 B2
APPLICATION NO. : 13/514322
DATED : December 9, 2014
INVENTOR(S) : Yu Yang It is certified that error appears in the above-identified patent and that said Letters Patent is hereby corrected as shown below:

In the Specification

Column 2
Line 14, after "Each" insert -- $R^1$ --.

Column 9
Line 18, delete "-trifluorethyl," and insert -- -trifluoroethyl, --, therefor.

Column 10
Line 7, delete "(VIc), (VIc)," and insert -- (VIc), --, therefor.

Column 11
Line 47, delete "(VIc), (VIc)," and insert -- (VIc), --, therefor.

Column 12
Line 6, delete "included" and insert -- include --, therefor.

Column 13
Line 17, delete "analkyl," and insert -- alkyl, --, therefor.

Column 16
Line 54, delete "of of" and insert -- of --, therefor.

In the Claims

Column 22
Line 54, in Claim 3, delete "thereof" and insert -- thereof; --, therefor.

Signed and Sealed this
Twenty-eighth Day of July, 2015

Michelle K. Lee
*Director of the United States Patent and Trademark Office*

CERTIFICATE OF CORRECTION (continued)
U.S. Pat. No. 8,907,120 B2

Column 23

Line 25, in Claim 6, delete "thereof" and insert -- thereof; --, therefor.

Line 37 (Approx.), in Claim 7, delete "$Y^2-(CO)-NR^2-Y^3-$" and insert -- $-Y^2-(CO)-NR^2-Y^3-$ --, therefor.

Column 24

Line 23, in Claim 9, delete "thereof" and insert -- thereof; --, therefor.

Line 31, in Claim 10, delete "thereof" and insert -- thereof; --, therefor.